United States Patent [19]
Carter

[11] Patent Number: 5,585,466
[45] Date of Patent: Dec. 17, 1996

[54] CRYSTALS OF SERUM ALBUMIN FOR USE IN GENETIC ENGINEERING AND RATIONAL DRUG DESIGN

[75] Inventor: Daniel C. Carter, Decatur, Ala.

[73] Assignee: The United States of America as represented by the Administrator of the National Aeronautics and Space Administration, Washington, D.C.

[21] Appl. No.: 351,861

[22] Filed: Dec. 6, 1994

[51] Int. Cl.⁶ .................. C07K 14/765; C07K 14/76; C07K 14/47; C07K 1/30
[52] U.S. Cl. .................. 530/363; 530/362; 530/364; 530/418; 530/419; 530/421; 530/829; 530/830
[58] Field of Search .................. 530/362, 363, 530/364, 829, 830, 418, 419, 421

[56] References Cited

U.S. PATENT DOCUMENTS 4,833,233  5/1989  Carter ........................ 530/363
4,886,646 12/1989  Carter et al. ................ 117/202

OTHER PUBLICATIONS

Ho et al. "X–Ray & Primary Structure of Horse Serum Albumin (Eguus caballus) at O.27nm Resolution" Fur. J. Biochem. 215 205–212 1993.

Primary Examiner—George C. Elliott
Assistant Examiner—Nancy J. Degen
Attorney, Agent, or Firm—Robert L. Broad, Jr.

[57] ABSTRACT

Serum albumin crystal forms have been produced which exhibit superior x-ray diffraction quality. The crystals are produced from both recombinant and wild-type human serum albumin, canine, and baboon serum albumin and allow the performance of drug-binding studies as well as genetic engineering studies. The crystals are grown from solutions of polyethylene glycol or ammonium sulphate within prescribed limits during growth times from one to several weeks and include the following space groups: $P2_1$, C2, P1.

24 Claims, 4 Drawing Sheets

CRYSTALS OF SERUM ALBUMIN FOR USE IN GENETIC ENGINEERING AND RATIONAL DRUG DESIGN

ORIGIN OF THE INVENTION

This invention was made by an employee of the United States Government and may be manufactured and used by or for the Government for governmental puposes without the payment of any royalties.

FIELD OF THE INVENTION

The present invention is related to the use of albumin in structural studies related to drug binding and genetic engineering and, more particularly, to high quality crystal forms prepared from human, baboon and canine serum albumin which are suitable for conducting drug and ligand binding experiments.

BACKGROUND OF THE INVENTION

Serum albumin, a protein of multiple functions and manifold applications, is one of the most extensively studied proteins in biochemistry. As the most abundant protein in the circulatory system and with typical blood concentrations of 5 g/100 ml, serum albumin contributes 80% to colloid osmotic blood pressure. In addition, it has now been determined that albumin is chiefly responsible for the maintenance of blood pH. It is located in every tissue and bodily secretion, with the extracellular protein comprising 60% of total albumin. In mammals, albumin is synthesized by the liver and possesses a half-life in circulation of 19 days. Complete amino acid sequences are known for bovine, rat, and human serum albumins.

While the principal function of serum albumin remains unknown, it is clear that serum albumin contributes to many transport and regulatory processes. Many studies have focused on the multi-functional binding properties of serum albumin to various metals, fatty acids, hormones, and a wide spectrum of therapeutic drugs. The majority of these binding studies have involved human serum albumin ("HSA") and many have shown that the distribution, free concentration, and metabolism of various pharmaceuticals can be significantly altered as a function of the magnitude of binding to HSA.

Serum albumin is the principal carrier of fatty acids that are otherwise insoluble in circulating plasma. But albumin performs many other functions as well, such as sequestering oxygen free radicals and inactivating various toxic lipophilic metabolites such as bilirubin. Although albumin has a broad affinity for small, negatively charged aromatic compounds, it has high affinities for fatty acids, hematin, and bilirubin. Additionally, it forms covalent adducts with pyridoxal phosphate cysteine, glutathione, and various metals, such as Cu(II), Ni(II) Hg(II), Ag(II), and Au(I).

It is widely accepted in the pharmaceutical industry that the overall distribution, metabolism, and efficacy of many drugs can be altered based on their affinity to serum albumin. In addition, many promising new drugs are rendered ineffective because of their unusually high affinity to serum albumin. Some studies have suggested that modified serum albumin may be used as a selective contrast agent for tumor detection and/or therapy. Other studies have demonstrated that albumin may be used to deliver toxic compounds for elimination of Mycobacterium tuberculosis via receptor-mediated drug delivery. Recently, chimeric albumin molecules such as HSA-CD4 and HSA-Cu,Zn-superoxide dismutase have been utilized to increase the half-life and distribution, and reduce the immunogenicity of these potential protein therapeutics.

In order to study the use of albumin in rational drug design, it is necessary to understand its structure and the chemistry of drug/ligand binding. The power of rational drug design has recently been reviewed by Bugg et al., *Drugs by Design,* 92 Scientific American (December, 1993). A requirement of rational drug design is the production of crystals of the desired target protein which provide for the determination of the detailed atomic structure of both the parent protein and its complex with the pharmaceutical. A tetragonal crystal form of human serum albumin, described in U.S. Pat. No. 4,833,233, provided means for the first atomic structure determination of human serum albumin. Consequently, this crystal form has been utilized to explain a great deal about serum albumin structure and chemistry particularly in regard to the mode of ligand binding taught by Carter & Ho, *Structure of Serum Albumin,* 45 Advances in Protein Chemistry 153 (1994). However, this crystal form has the disadvantage of an intrinsic limit on the diffraction data, namely to 2.9 angstroms and limited stability under x-irradiation.

SUMMARY OF THE INVENTION

Thus, it is a purpose of the present invention to overcome the disadvantage of the prior art and thereby provide high quality crystals of serum albumin.

In accordance with a preferred embodiment of the invention human serum albumin crystals are prepared which exhibit x-ray diffraction resolutions to d-spacings of 2.4 angstroms (Å) or less. In a preferred form, the crystals have a monoclinic space group $P2_1$, and the following unit cell constants a=58.9 (7), b=88.3 (7), c=60.7 (7) and Beta=101 (2) degrees. The crystals are prepared from recombinant or naturally isolated serum albumin.

In another preferred embodiment, canine albumin crystals ("CSA") are prepared which exhibit x-ray diffraction resolutions to d-spacings of 2.2 angstroms or less.

It is, therefore, an object of the present invention to provide serum albumin crystals for studies directed toward improving the efficacy, delivery or metabolism of various high potential pharmaceuticals that are rendered ineffective by serum albumin.

This and other objects of the present invention will become apparent from the detailed description to follow.

BRIEF DESCRIPTION OF THE DRAWINGS

There follows a detailed description of the preferred embodiments of the present invention which are to be taken together with the accompanying drawings, wherein.

DESCRIPTION OF THE PREFERRED EMBODIMENT

Figure 1:
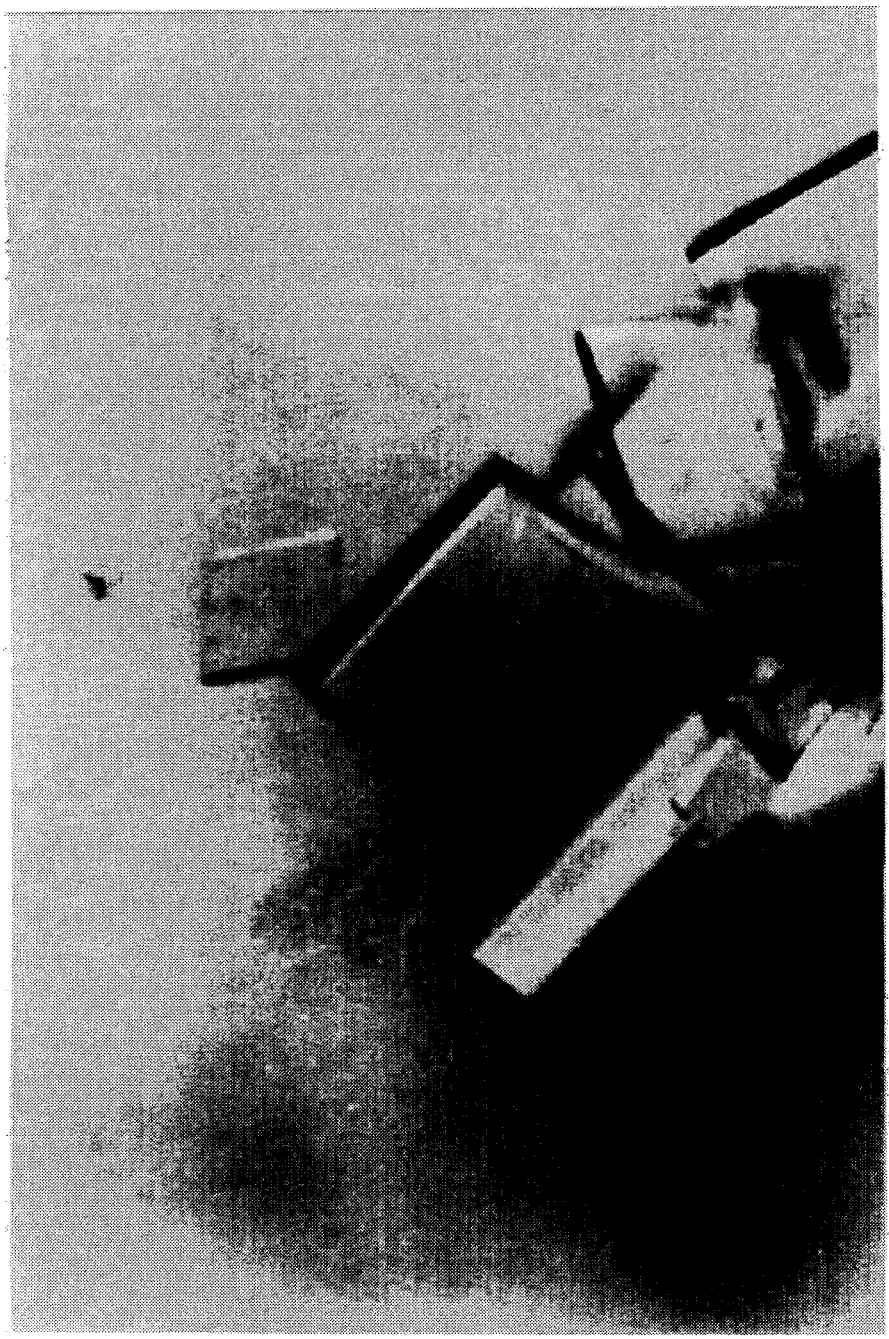
FIG. 1 is a photograph showing one of the crystal forms (Form I) of HSA embodying the present invention.

Monoclinic plate-like crystals of human serum albumin in accordance with the method of the present invention are grown from a precipitant solution of polyethylene glycol ("PEG"), and a buffer, with concentration of reagents and pH being carefully controlled within prescribed limits. Any of the three basic techniques generally used for growth of protein crystals, that is, "hanging-drop" or vapor diffusion, dialysis and batch methods may be employed. The hanging-drop method is, however, preferred.

Further, either recombinant HSA or naturally isolated HSA may be used for crystal growth.

In the hanging drop method a small drop of protein solution is placed on a cover slip, or glass plate, which is inverted over a well of solution and sealed. The solution in the well contains a precipitating agent, which is also present in a lesser amount in the protein droplet. The function of the precipitating agent is twofold. First, the solution in the well is initially at a lower vapor pressure than the protein droplet so that evaporation progresses at a rate fixed by the difference in the vapor pressures and the distance by which the vapor, usually water, must diffuse. Second, the precipitating agent lowers the solubility of the protein in solution by competing with the protein for available solvent. Thus, as evaporation from the protein droplet occurs, the solution becomes supersaturated in protein. Under the appropriate conditions including pH, protein concentration and temperature, crystallization of the protein or macromolecule then occurs.

A stock solution of PEG is prepared by combining 50 weight percent PEG having a molecular weight on the order of 3350 grams/mole with 50 weight percent water. The precipitant solution is then prepared by mixing the stock solution with an appropriate buffer (usually 0.05 molar) to adjust the pH and starting concentration. Appropriate buffers include sodium acetate, sodium citrate and Tris (hydroxymethyl) aminomethanemaleate and potassium phosphate. However, monobasic sodium phosphate ($NaHPO_4$) is the preferred buffer. As a general guideline for preparing the precipitant solution, 35 weight percent of the stock solution is combined with 65% of the phosphate buffer which has a pH between 4.6 and 8.0. Most preferably, the buffer solution remains neutral, that is, pH 7.5.

Once the precipitant solution is prepared, additional pH adjustments may be required to compensate for variations in pH which can arise from variations in molecular weight and residue content of PEG. These adjustments are carried out by adding small amounts of a base such as potassium hydroxide or an acid such as hydrochloric acid to the precipitant solution. If the hanging-drop method is employed for crystal growth, the droplet is preferably formed using 10 microliters (μl) of the precipitant solution and 10 μl of HSA having a concentration of 90 to 200 mg/ml, preferably 120 mg/ml. The droplet is sealed in a chamber and equilibrated over a 1 ml reservoir solution of the precipitant solution. Within ten days to three weeks, crystals appear and reach sizes of up to 0.7 mm in the largest dimension, with total dimensions being on the order of 0.7 mm×0.15 mm×0.2 mm.

Figure 2:
FIG. 2 is a photograph showing another one of the crystal forms (Form II) of HSA embodying the present invention.

HSA crystals appear in two forms. FIG. 1 is a photograph showing the Form I crystals which typically appear before the more preferred, Form II crystals. The Form I crystals are less mechanically stable and exhibit poorer diffraction characteristics. FIG. 2 is a photograph showing the Form II crystals which grow in the monoclinic space group $P2_1$ and possesses the following unit cell constants: a=58.9 (7), b=88.3 (7), c=60.7 (7), Beta=101 (2) degrees.

The quality of protein crystals is determined by the ability of the crystal to scatter x-rays of wavelengths (typically 1.0 to 1.6 Å) suitable to determine the atomic coordinates of the protein. The measure of the quality is determined as a function of the highest angle of scatter (the ultimate or intrinsic resolution) and according to Bragg's Law: $n\lambda=2d\sin\theta$, d may be determined, and represents the resolution of the crystal form in angstroms. Thus, this measurement is routinely used to judge the ultimate usefulness of protein crystals. The International Union of Crystallographers has determined that there are 230 unique ways in which chemical substances, proteins or otherwise, may assemble in three-dimensions to form crystals. These are called the 230 "space groups." The designation of the space group in addition to the unit cell constants (which define the explicit size and shape of the cell which repeats within the crystal) is routinely used to uniquely identify a crystalline substance. Certain conventions have been established to ensure the proper identification of crystalline materials and these conventions have been set forth and documented in the International Tables for Crystallography, incorporated herein by reference.

High quality crystals of baboon serum albumin ("BbSA") are prepared under identical conditions to those for human serum albumin. The crystals grow in the monoclinic space group $P2_1$ possess substantially the same unit cell constants as the HSA crystals. The BbSA forms can be used as substitutes in studies of human drug/albumin interactions where crystallization of the complexes are only possible with this species. The principles of this application has been convincingly demonstrated at the atomic level by Ho et al., *X-ray and primary structure of horse serum albumin* (Equus caballus) *at 0.27-nm resolution*, 215 Eur. J. Biochem. 205 (1993) in the comparison of the ligand binding properties of horse serum albumin with human serum albumin, and by Carter and Ho, supra. Thus, the precise atomic interactions between protein and ligand can only be provided by a determination of the corresponding crystal structure. Although most of the important key residues involved in ligand binding by albumin are conserved among the various species, there can also exist selective differences in albumin ligand binding chemistry between species as discussed in C. F. Chignell, 2 *CRC Handbook of Biochemistry and Molecular Biology*, 554–582 (1976).

Figure 3:
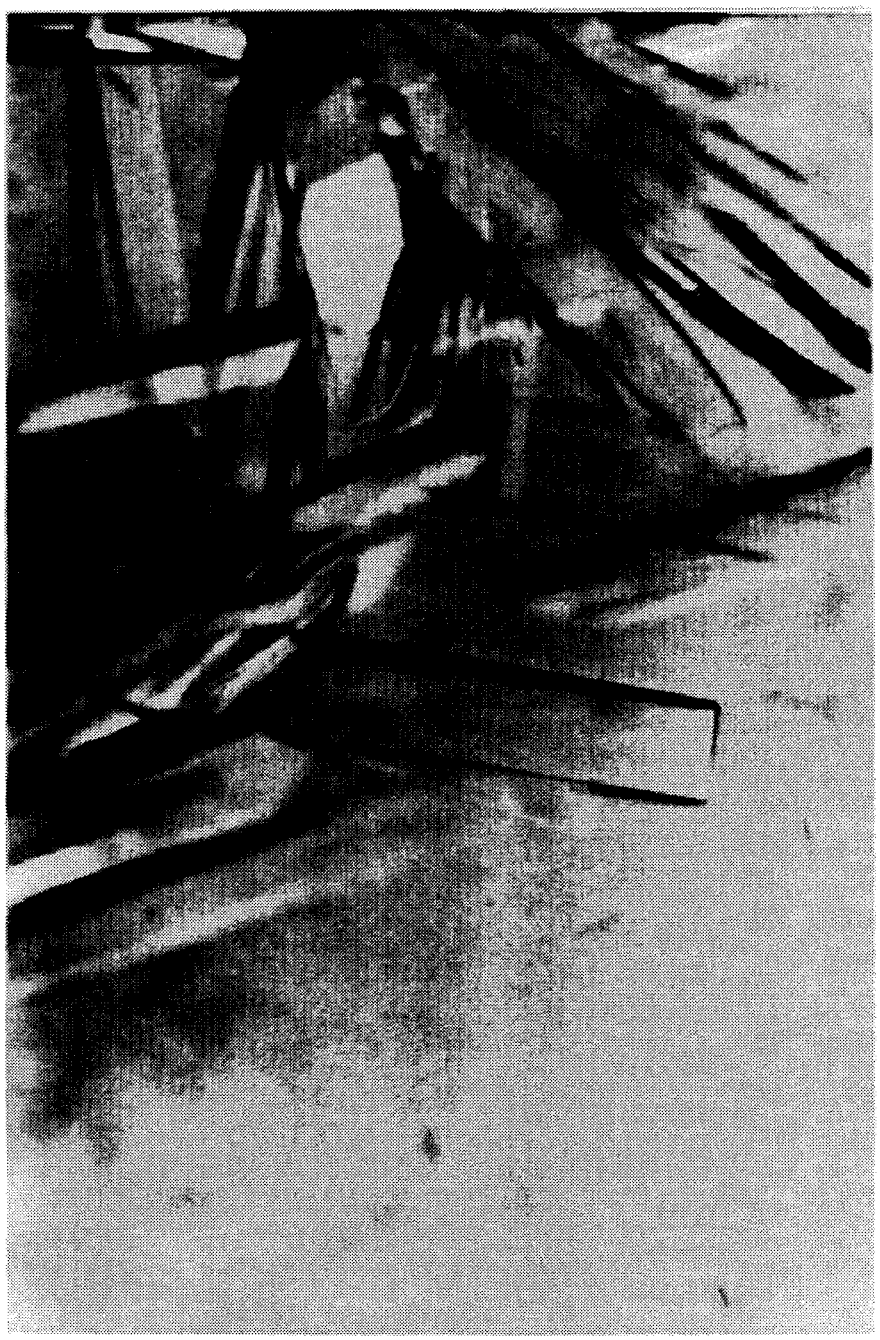
FIG. 3 is a photograph showing high quality crystals of CSA, space group P1.

FIG. 3 is a photograph showing high quality crystals of CSA. The crystals possess the following unit cell constants: a=51.7 (7) A, b=66.6 (7) A, c=108.1 (9) A, alpha=90.4 (9), beta=107.9 (9), gamma=93.1 (9) degrees. These crystals were grown using a hanging-drop method with 56–60% volume/volume (v/v) saturated ammonium sulphate solution. Appropriate buffers for preparing CSA crystals include TRIS, cacodylate, citrate phosphate and potassium phosphate. However, the preferred buffer is $KHPO_4$ at pH 7.5 to 8.0. The droplet was prepared using 10 μl of the precipitant solution and 10 μl of CSA having a concentration of 180 mg/ml, although CSA crystals may be grown with lower protein concentration. The resulting crystals exhibited x-ray diffraction resolutions to d-spacings less than 2.2 angstroms, thereby providing a means for high resolution studies of drug/ligand interaction with albumin. Both baboon and canine serum albumin are important in drug efficacy, and delivery, i.e., rational drug design, because they represent important animal models for human efficacy trials. In particular, differences in the chemistry of drug binding between albumins often reflects important differences in their respective albumins, as taught by Carter & Ho, supra. This difference is reflected in their primary structures. Thus, an understanding of these interactions may provide further insight in future studies of new promising pharmaceuticals in human trials. Similarly their different chemistries also provide other avenues in genetic engineering studies and the production of novel albumin based therapeutics.

To obtain structural information about the protein/drug interaction to allow rational drug design, it is also necessary to prepare a crystal of the complex, the complex being the drug bound to the serum albumin. Crystals of the complex can be produced using two different methods. In a first method, the actual complex itself is crystallized using the prescribed conditions set forth for the native serum albumin(s), i.e., HSA, BbSA or CSA. Once crystals of suitable size have grown, x-ray diffraction data are collected. This process usually involves the measurements of many tens of thousands of diffracted x-rays over a period of one to several days depending on the crystal form and the resolution of the data required. According to the method, crystals are bombarded with x-rays. The crystals diffract the rays, creating a geometrically precise splatter of spots on photographic film or electronic detectors. The distribution of atoms within the crystal influences the pattern of spots. Subtraction of the data, $F_{ligand} - F_{native}$, using phases from the atomic model of the albumin structure produces the electron density of only the drug molecule. Visualization of the observed electron density superimposed on the atomic coordinates derived from the same crystal form provides a determination of key protein drug interactions that are necessary for rational drug design. In the normal practice of the invention, this would be an iterative process involving several cycles of modeling with each of the new drugs synthesized as a result of the changes suggested by the crystal structure of the complex. In the second commonly practiced method, the drugs or ligands may be soaked into the crystal because of the inherently large aqueous solvent channels present in protein crystals. (See, e.g., Carter et al., 244 Science, 1195–1198 (1989).) The crystalline complex thus formed follows the same procedure described above to provide the electron density of the drug of interest. The difference in the genetic engineering studies is that there is no complex formed. Instead, a crystal of the genetically altered albumin is grown by the prescribed methods, the x-ray data is collected, the resulting structure is refined by any of a variety of known methods, and the desirable or undesirable consequences of the engineered change is assessed by direct comparison with the atomic structure of the native molecule.

In another preferred embodiment of the invention, long chain fatty acids are added to the HSA in ratios. The phrase "long chain fatty acids" is used to define any of the common saturated or unsaturated fatty acids such as palmitic, eicon, myristic and lauric acid. Furthermore, addition of propionic acid and caprylic acid in trace amounts from less than 0.1 to 2 mole fatty acid/mole HSA may enhance the production of favorable crystal form (Form II).

Figure 4:
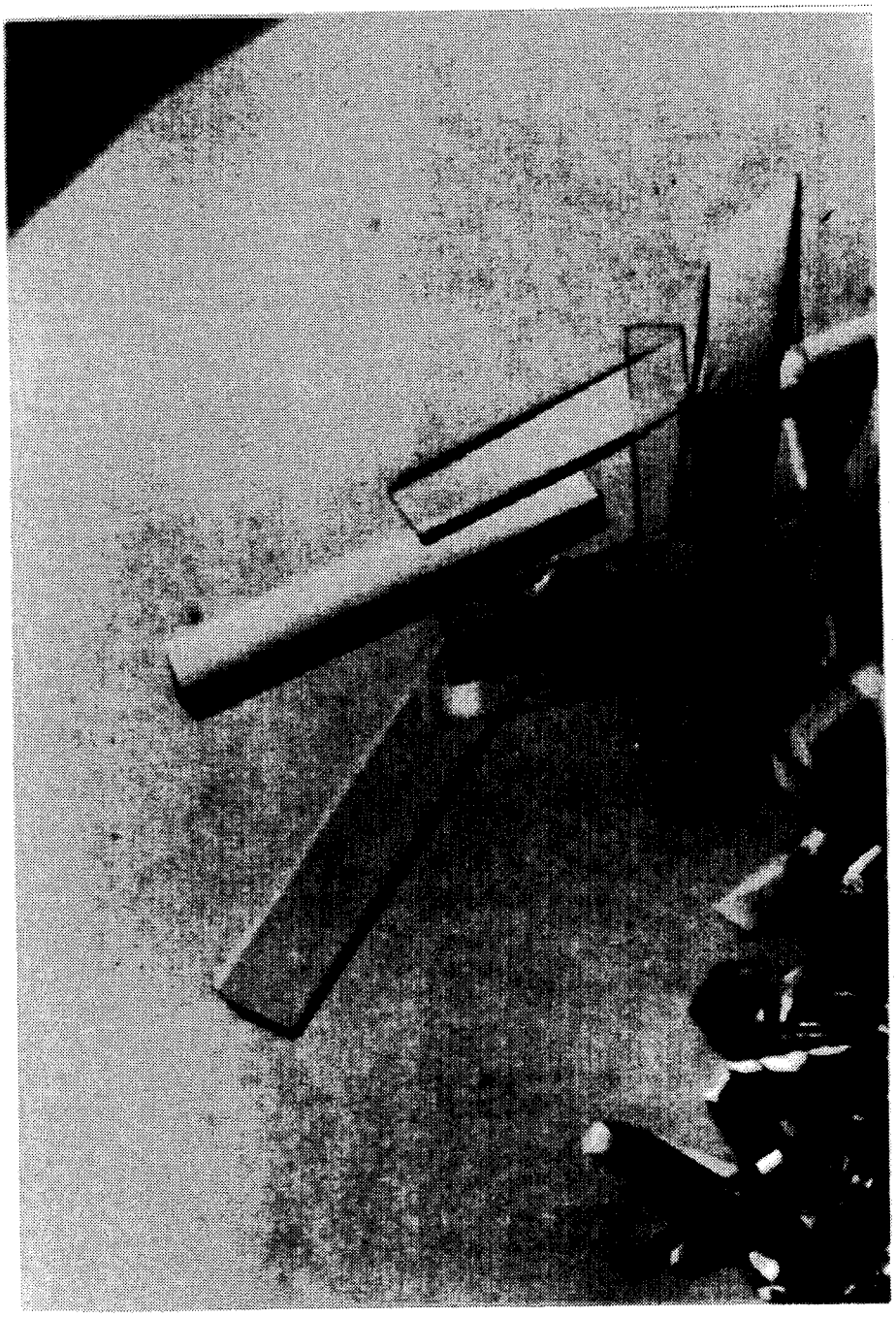
FIG. 4 is a photograph showing high quality crystals of HSA containing from 3 to 10 molar excess of long chain fatty acid, monoclinic space group C2 (Form III).

FIG. 4 is a photograph showing high quality crystals of HSA containing from 3 to 10 molar excess of long chain fatty acid. These crystals produce a new crystal form, Form III, which, like the BbSA and CSA crystals, also exhibits favorable diffraction properties as indicated in the table below. As will be apparent by the examination of Table 1, the serum albumin crystals described herein represent very high quality and can be reproducibly grown.

TABLE 1

CRYSTAL DATA ON THE POLYMORPHS OF SERUM ALBUMIN

| Crystal System: | Monoclinic | Monoclinic | Monoclinic | Orthorhombic | Orthorhombic | Tetragonal | Tetragonal |
|---|---|---|---|---|---|---|---|
| Space Group: | C2 | $P2_1$ | C2 | $P2_12_12_1$ | $P2_12_12$ | $P4_12_12$ or $P4_32_12$ | $P42_12$ |
| Unit Cell Dimensions (nm) | a = 187.2<br>b = 39.0<br>c = 96.9<br>β = 105.0 | a = 58.9<br>b = 88.3<br>c = 60.7<br>β = 101.9 | a = 126.5<br>b = 39.2<br>c = 135.2<br>β = 93.3 | a = 155.0<br>b = 83.0<br>c = 122.0 | a = 137.3<br>b = 275.0<br>c = 58.02 | a = 84.0<br>c = 276.0 | a = 187.0<br>b = 81.0 |
| Solvent Content: | 35% | 33% | 51% | 52% | 59% | 54% | 78% |
| n: | 118,130 | 66,492 | | | | | |
| u: | 21,037 | 23,502 | | | | | |
| Rmerge: | 6.1% | 4.6% | | | | | |
| Molecules per Asymmetric Unit | 1 | 1 | 1* | 2* | 3* | 1* | 1 |
| Diffraction Limits (Å) | 2.4 | 2.35 | 2.5 | 3.7 | 3.0 | 3.8 | 2.9 |
| Protein: | HSA (Form III) | HSA (Form II) | HSA | HSA | HSA | HSA | HSA |
| References: | this work | this work | (1) | (1) | (2) | (1) | (3,4) |

| Crystal System: | Hexagonal | Triclinic | Monoclinic |
|---|---|---|---|
| Space Group: | $P6_1$ | P1 | $P2_1$ |
| Unit Cell Dimensions (nm) | a = 96.2<br>c = 144.0<br>α = 90.4<br>β = 107.9<br>γ = 93.1 | a = 51.7<br>b = 66.6<br>c = 108.1<br>β = 100.4 | a = 59.0<br>b = 86.9<br>c = 60.5 |
| Solvent content: | 43% | 28% | 33% |
| n: | | 123,203 | 16,355 |
| u: | | 42,780 | 8,472 |
| Rmerge: | | 10.2% | 8.3% |
| Molecules per Asymmetric | 1 | 2 | 1 |

TABLE 1-continued

CRYSTAL DATA ON THE POLYMORPHS OF SERUM ALBUMIN

| Unit: Diffraction Limits: (A) | 2.7 | 2.2 | 2.7 |
|---|---|---|---|
| Protein: | ESA | CSA | BbSA |
| References: | (1,5) | This work | This work | n: total number of reflections measured;
u: number of unique reflections
Rmerge: $|<I_{hkl}> - I_{hkl}|/<I_{hkl}>$;
*: based on published preliminary estimates.
1. R. J. McClure and B. M. Craven, 239 J. Mol. Bio. 845–849 (1974).
2. S. N. Rao et al. 251 J. Biol. Chem. 3191–3193 (1976).
3. D. C. Carter, et al., 244 Science 1195–1198 (1989).
4. D. C. Carter, U.S. Pat. No. 4,833,233.
5. J. X. Ho et al., 215 Eur, J. Biochem. 201–212, (1993).

Other co-crystallization complexes have also been formed with iodinated fatty acid of lauric acid and numerous chemically diverse ligands, such as bilirubin, hematin and warfarin with suitable diffraction quality with reflections measured less than 2.8 angstrom resolution.

Although the invention has been described in considerable detail with respect to preferred embodiments thereof, variations and modifications will be apparent to those skilled in the art without departing from the spirit and scope of the invention as set forth in the claims.

We claim:

1. A method of growing crystals of serum albumin comprising the steps of:

providing an aqueous solution of serum albumin having a concentration of 10 to 220 milligrams per milliliter;

providing an aqueous precipitant solution comprising polyethylene glycol having a concentration of 17–30% (v/v) and a molecular weight of 2000 to 8000 and a corresponding buffer solution;

mixing a droplet of said aqueous serum albumin solution with a droplet of said precipitant solution;

suspending the resulting mixed droplet over a well of precipitant solution in a sealed container, the vapor pressure of the solution in said well being lower than the vapor pressure in the resulting mixed droplet; and allowing the suspended mixed droplet to stand for a period of time such that a serum albumin crystal in said mixed droplet grows to a predetermined size.

2. The method according to claim 1 wherein the buffer solution comprises a monobasic potassium phosphate solution.

3. The method according to claim 1 wherein the concentration of said aqueous serum albumin solution is approximately 120 milligrams per milliliter.

4. The method according to claim 1 wherein the polyethylene glycol has an average molecular weight of 3350.

5. The method according to claim 1 wherein said polyethylene glycol is combined with said corresponding buffer solution having a pH of 6.8 to 7.8.

6. The method according to claim 5 wherein said serum albumin comprises human serum albumin.

7. The method according to claim 6 further comprising the step of adding a long chain fatty acid to the precipitant solution in molar ratios of 0.1 to 10 per human serum albumin molecule.

8. The method according to claim 5 wherein said serum albumin comprises baboon serum albumin.

9. The method according to claim 8 further comprising the step of adding a long chain fatty acid to the precipitant solution in molar ratios of 0.1 to 10 per baboon serum albumin molecule.

10. The method according to claim 1 wherein the aqueous precipitant solution comprises saturated ammonium sulfate having a concentration of 35–50% (v/v).

11. The method according to claim 10 wherein the corresponding buffer solution has a pH of 7.2 to 8.2.

12. The method according to claim 11 wherein said serum albumin comprises canine serum albumin.

13. The method according to claim 12 further comprising the step of adding long chain fatty acids to the precipitant solution in molar ratios of 0.1 to 2 per canine serum albumin molecule.

14. A serum albumin crystal prepared by the method of claim 1, wherein the serum albumin is selected from the group consisting of human serum albumin, baboon serum albumin and canine serum albumin.

15. A method of growing crystals of serum albumin comprising the steps of:

providing an aqueous solution of serum albumin having a concentration of 10 to 120 milligrams per milliliter;

providing an aqueous precipitant solution comprising polyethylene glycol having a concentration of 17–30% (v/v) and a molecular weight of 2000 to 8000 and a corresponding buffer;

combining said serum albumin solution with said precipitant solution and allowing the combined solution to stand for a predetermined time until a serum albumin crystal therein grows to a predetermined size.

16. The method according to claim 15 wherein said serum albumin solution is disposed within a semipermeable size exclusion membrane and said precipitant solution is combined with the serum albumin solution by diffusion through said membrane.

17. The method according to claim 15 wherein said step of combining precipitant solution comprises slowly adding the serum albumin solution to the precipitant solution, sealing the resulting solution in a container and allowing the resulting solution to stand.

18. The method according to claim 15 wherein said corresponding buffer solution has a pH of 6.5 to 8.0.

19. The method according to claim 18 wherein said serum albumin comprises human serum albumin.

20. The method according to claim 18 wherein said serum albumin comprises baboon serum albumin.

21. The method according to claim 18 wherein the aqueous precipitant solution comprises 50–70% (v/v) saturated ammonium sulfate solution.

22. The method according to claim 21 wherein said corresponding buffer solution has a pH of 7.0 to 8.2.

23. The method according to claim 22 wherein said serum albumin comprises canine serum albumin.

24. A serum albumin crystal prepared by the method of claim 15, wherein the serum albumin is selected from the group consisting of human serum albumin, baboon serum albumin and canine serum albumin.

* * * * *